United States Patent
Gschneidner et al.

(10) Patent No.: US 7,297,794 B2
(45) Date of Patent: *Nov. 20, 2007

(54) PHENOXY AMINE COMPOUNDS AND COMPOSITIONS FOR DELIVERING ACTIVE AGENTS

(75) Inventors: David Gschneidner, Thornwood, NY (US); Kelly Kraft, Hopewell Junction, NY (US); Chen Zhu, Berkeley Heights, NJ (US); Yi Chen, Cheshire, CT (US)

(73) Assignee: Emisphere Technologies, Inc., Tarrytown, NY (US)

( * ) Notice: Subject to any disclaimer, the term of this patent is extended or adjusted under 35 U.S.C. 154(b) by 130 days.

This patent is subject to a terminal disclaimer.

(21) Appl. No.: 10/495,797

(22) PCT Filed: Nov. 13, 2002

(86) PCT No.: PCT/US02/36552

§ 371 (c)(1),
(2), (4) Date: Aug. 12, 2004

(87) PCT Pub. No.: WO03/045306

PCT Pub. Date: Jun. 5, 2003

(65) Prior Publication Data

US 2005/0119502 A1    Jun. 2, 2005

Related U.S. Application Data

(60) Provisional application No. 60/357,288, filed on Feb. 15, 2002, provisional application No. 60/350,488, filed on Nov. 13, 2001.

(51) Int. Cl.
C07D 295/03 (2006.01)
C07D 233/58 (2006.01)
C07C 215/46 (2006.01)
A61K 31/535 (2006.01)
A61K 31/415 (2006.01)
A61K 31/135 (2006.01)

(52) U.S. Cl. .................. 544/174; 548/341.1; 564/353; 514/239.2; 514/399; 514/651

(58) Field of Classification Search ..................... None
See application file for complete search history.

(56) References Cited

U.S. PATENT DOCUMENTS 5,023,253 A    6/1991  Remers et al.

2005/0119502 A1    6/2005  Gschneidner et al.
2005/0277621 A1    12/2005  Gschneidner

FOREIGN PATENT DOCUMENTS

| EP | 0 274 867 A2 | 7/1988 |
| EP | 0 276 065 B1 | 6/1990 |
| EP | 0 407 217 A1 | 1/1991 |
| GB | 1 524 260 B1 | 9/1978 |
| JP | 58-113178 A1 | 7/1983 |
| JP | 04-041472 A1 | 2/1992 |
| JP | 04-117461 A1 | 4/1992 |
| WO | WO 01/32596 A1 | 5/2001 |
| WO | WO-2006/072070 | 7/2006 |

OTHER PUBLICATIONS

Database CAPLUS on STN, Acc. No. 2001:93069, Hacking et al., Journal of Molecular Catalysis B: Enzymatic (2001), 11(4-6), p. 315-321 (abstract).*
Database CAPLUS on STN, Acc. No. 1955:56721, Wright et al., Journal of the American Chemical Society (1954), 76, p. 4396-8 (abstract).*
Database CAPLUS on STN, Acc. No. 1960:74251, Colonge et al., Bulletin de la Societe Chimique de France (1959), p. 817-19 (abstract).*
Abood, L.G., et al., "Chemical Constitution and Biochemical Correlates of Aryloxyalkylpiperazines", Arch. Intern. Pharmacodynamie (1961), 134, pp. 106-130.
Hanna, Patrick E., et al., "Leukotriene Receptor Antagonists. 1. Synthesis and Structure-Activity Relationships of Alkoxyacetophenone Derivatives", Journal of Medicinal Chemistry, (1987) vol. 30(4), pp. 682-689.
Herron, David K., et al., "Leukotriene B4 Receptor Antagonists: The LY255283 Series of Hydroxyacetophenones", Journal of Medicinal Chemistry, May 15, 1992, vol. 35, No. 10, pp. 1818-1828.
Buzas, et al., Ethers of thymol and carvacrol. Bull. Soc. Chim. France (1959), pp. 839-849.
Results from a Chemical Structure Search dated Oct. 2001.
Results from a Chemical Structure Search dated Dec. 2006.
Sami, et al., Preparation and Antitumor Activity of Additional Mitomycin A Analogues, J. Med. Chem. 1989, 32, 703-708.

* cited by examiner

Primary Examiner—Brian Davis
(74) Attorney, Agent, or Firm—Darby & Darby P.C.

(57) ABSTRACT

Phenoxy amine compounds and compositions for the delivery of active agents are provided. Methods of administration and preparation are provided as well.

44 Claims, No Drawings

PHENOXY AMINE COMPOUNDS AND COMPOSITIONS FOR DELIVERING ACTIVE AGENTS

This application claims the benefit of U.S. Provisional Application No. 60/350,488, filed Nov. 13, 2001, and U.S. Provisional Application No. 60/357,288, filed Feb. 15, 2002, both of which are hereby incorporated by reference.

FIELD OF THE INVENTION

The present invention relates to phenoxy amine compounds for delivering active agents, such as biologically or chemically active agents, to a target. These compounds are well suited for forming non-covalent mixtures with active agents for oral, intracolonic, pulmonary, and other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastrointestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; and 5,866,536.

More recently, a polymer has been conjugated to a modified amino acid or a derivative thereof via a linkage group to provide for polymeric delivery agents. The modified polymer may be any polymer, but preferred polymers include, but are not limited to, polyethylene glycol (PEG), and derivatives thereof. See, for example, International Patent Publication No. WO 00/40203.

International Patent Publication Nos. WO 01/32130 and WO 01/32596 disclose particular phenyl amine carboxylic acid compounds and phenoxy carboxylic acid compounds for delivering active agents. International Publication No. WO 00/50386 also discloses amine delivery agents.

However, there is still a need for simple, inexpensive delivery systems which are easily prepared and which can deliver a broad range of active agents by various routes.

SUMMARY OF THE INVENTION

The present invention provides compounds and compositions which facilitate the delivery of active agents. Delivery agent compounds of the present invention include those having the following formula:

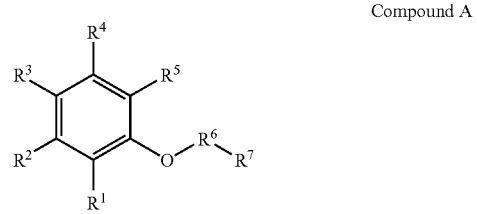

Compound A or a salt thereof wherein (a) $R^1$, $R^2$, $R^3$, and $R^4$ are independently H, —OH, halogen, $C_1$-$C_4$alkyl, $C_1$-$C_4$ alkenyl, $C_1$-$C_4$alkoxy, —C(O)$R^8$, —NO$_2$, —NR$^9$R$^{10}$, or —N$^+$R$^9$R$^{10}$R$^{11}$ (Y$^-$);

$R^8$ is hydrogen, —OH, $C_1$-$C_6$ alkyl, $C_1$-$C_4$ alkyl substituted with halogen or —OH, $C_2$-$C_4$ alkenyl unsubstituted or substituted with halogen or —OH, or —NR$^{14}$R$^{15}$;

$R^9$, $R^{10}$, and $R^{11}$ are independently hydrogen, oxygen, $C_1$-$C_4$ alkyl unsubtituted or substituted with halogen or —OH, $C_2$-$C_4$ alkenyl unsubstituted or substituted with halogen or —OH;

Y is halide, hydroxide, sulfate, nitrate, phosphate, alkoxy, perchlorate, tetrafluoroborate, carboxylate, mesylate, fumerate, malonate, succinate, tartrate, acetate, gluconate, maleate;

$R^5$ is H, —OH, —NO$_2$, halogen, CF$_3$, —NR$^{14}$R$^{15}$, —N$^+$R$^{14}$R$^{15}$R$^{16}$ (Y$^-$), amide, $C_1$-$C_{12}$ alkoxy, $C_1$-$C_{12}$ alkyl, $C_2$-$C_{12}$ alkenyl, carbamate, carbonate, urea, or —C(O)R$^{22}$; $R^5$ is optionally substituted with halogen, —OH, —SH, or —COOH; $R^5$ is optionally interrupted by O, N, S, or —C(O)—;

$R^{14}$, $R^{15}$, and $R^{16}$ are independently H or $C_1$-$C_{10}$ alkyl;

$R^{22}$ is H, $C_1$-$C_6$ alkyl, —OH, —$NR^{14}R^{15}$;

$R^6$ is substituted or unsubstituted $C_1$-$C_{16}$ alkylene, $C_2$-$C_{16}$ alkenylene, $C_2$-$C_{16}$ alkynylene, $C_5$-$C_{16}$ arylene, ($C_1$-$C_{16}$ alkyl) arylene or aryl($C_1$-$C_{16}$ alkylene); $R^6$ is optionally substituted with $C_1$-$C_7$ alkyl or $C_1$-$C_7$ cycloalkyl;

$R^7$ is —$NR^{18}R^{19}$ or —$N^+R^{18}R^{19}R^{20}Y^-$;

$R^{18}$ and $R^{19}$ are independently hydrogen, oxygen, hydroxy, substituted or unsubstituted $C_1$-$C_{16}$ alkyl, substituted or unsubstituted $C_2$-$C_{16}$ alkenyl, substituted or unsubstituted $C_2$-$C_{16}$ alkynyl, substituted or unsubstituted aryl, substituted or unsubstituted alkylcarbonyl (e.g. substituted or unsubstituted ($C_{1-6}$ alkyl)carbonyl), substituted or unsubstituted arylcarbonyl, substituted or unsubstituted alkanesulfinyl (e.g. substituted or unsubstituted ($C_{1-6}$ alkane)sulfinyl), substituted or unsubstituted arylsulfinyl, substituted or unsubstituted alkanesulfonyl (e.g. substituted or unsubstituted ($C_{1-6}$ alkane)sulfonyl), substituted or unsubstituted arylsulfonyl, substituted or unsubstituted alkoxycarbonyl (e.g. substituted or unsubstituted ($C_{1-6}$ alkoxy)carbonyl), or substituted or unsubstituted aryloxycarbonyl, or substituted or unsubstituted $C_5$-$C_7$ heterocyclic ring (i.e., 5, 6, or 7-membered heterocyclic ring), wherein the substitutions may be halogen or —OH; and $R^{20}$ is independently hydrogen, substituted or unsubstituted $C_1$-$C_{16}$ alkyl, substituted or unsubstituted $C_2$-$C_{16}$ alkenyl, substituted or unsubstituted $C_2$-$C_{16}$ alkynyl, substituted or unsubstituted aryl, substituted or unsubstituted alkylcarbonyl (e.g. substituted or unsubstituted ($C_{1-6}$ alkyl)carbonyl), substituted or unsubstituted arylcarbonyl, substituted or unsubstituted alkanesulfinyl (e.g. substituted or unsubstituted ($C_{1-6}$ alkane)sulfinyl), substituted or unsubstituted arylsulfinyl, substituted or unsubstituted alkanesulfonyl (e.g. substituted or unsubstituted ($C_{1-6}$ alkane)sulfonyl), substituted or unsubstituted arylsulfonyl, substituted or unsubstituted alkoxycarbonyl (e.g. substituted or unsubstituted ($C_{1-6}$ alkoxy)carbonyl), or substituted or unsubstituted aryloxycarbonyl; or (b) $R^1$-$R^{16}$ and $R^{20}$ are as defined above; and $R^{18}$ and $R^{19}$ combine to form a 5, 6, or 7-membered heterocyclic ring optionally interrupted with an oxo group and unsubstituted or substituted with $C_1$-$C_6$ alkyl, $C_1$-$C_6$ alkoxy, aryl, aryloxy, or carbocyclic ring.

According to one preferred embodiment, $R^7$ is morpholino, morpholinium salt, or diethanolamino.

According to another preferred embodiment, $R^6$ is a $C_1$-$C_{16}$ alkylene and $R^7$ is morpholino or a morpholinium salt. Preferably, $R^6$ is $C_4$-$C_{12}$ alkylene, such as an unsubstituted $C_4$-$C_{12}$ alkylene. More preferably, $R^6$ is $C_4$-$C_{10}$, $C_4$-$C_8$, or $C_6$-$C_8$ alkylene, such as an unsubstituted $C_4$-$C_{10}$, $C_4$-$C_8$, or $C_6$-$C_8$ alkylene. According to one embodiment, one of $R^1$-$R^5$ is hydroxy, for example, $R^1$ can be hydroxy.

According to one embodiment, when $R^6$ is a $C_1$-$C_{10}$ alkylene, at most one of $R^2$ and $R^4$ is halogen. According to another embodiment, $R^6$ is a $C_8$-$C_{16}$, $C_9$-$C_{16}$, $C_{10}$-$C_{16}$, or $C_{11}$-$C_{16}$ alkylene. For instance, $R^6$ may be a $C_8$, $C_9$, $C_{10}$, $C_{11}$, or $C_{12}$ alkylene (e.g., a normal $C_8$-$C_{12}$ alkylene). According to yet another embodiment, at most one of $R^1$ and $R^5$ is alkyl.

In one preferred embodiment, $R^1$=—OH and $R^2$=$R^3$=$R^4$=$R^5$=H or halogen.

In another preferred embodiment, $R^2$=—OH and $R^1$=$R^3$=$R^4$=$R^5$=H or halogen.

In another preferred embodiment, $R^3$=—OH and $R^1$=$R^2$=$R^4$=$R^5$=H or halogen.

In another preferred embodiment, halogen is F, Cl or Br, more preferably F or Cl, and more preferably Cl.

In another preferred embodiment, $R^6$=$C_1$-$C_{16}$ alkylene, ($C_1$-$C_{16}$ alkyl)arylene or aryl($C_1$-$C_{16}$ alkylene). More preferably $R^6$ is $C_1$-$C_{12}$ alkylene, more preferably $C_3$-$C_{10}$ alkylene, more preferably $C_4$-$C_{10}$ or $C_4$-$C_8$ alkylene, and more preferably $C_6$-$C_8$ alkylene. More preferably, $R^6$ is unsubstituted.

In another preferred embodiment, $R^7$=—$NR^{18}R^{19}$ and $R^{18}$ and $R^{19}$ are independently $C_1$-$C_4$ alkyl (e.g., methyl, ethyl, propyl, or butyl) substituted with —OH. In another preferred embodiment, $R^7$=—$NR^{18}R^{19}$ and $R^{18}$ and $R^{19}$ combine to form a six membered heterocyclic ring substituted with an oxo group.

According to one preferred embodiment, $R^1$ is hydrogen; $R^2$, $R^3$, and $R^4$ are independently hydrogen, halogen, —OH, or —$OCH_3$; $R^5$ is hydrogen, —OH, or —$C(O)CH_3$; $R^6$ is $C_1$-$C_{12}$ alkylene, and $R^7$ is $NR^{18}R^{19}$ wherein $R^{18}$ and $R^{19}$ combine to form a 5, 6, or 7 membered heterocyclic ring.

According to another preferred embodiment, one of $R^3$, $R^4$, and $R^5$ is hydroxy and the others are independently halogen or hydrogen; $R^1$ and $R^2$ are independently halogen or hydrogen; $R^6$ is $C_1$-$C_{16}$ alkylene; and $R^7$ is $NR^{18}R^{19}$ wherein $R^{18}$ and $R^{19}$ combine to form a 5, 6, or 7 membered heterocyclic ring. $R^6$ is preferably $C_6$-$C_{16}$, $C_6$-$C_{10}$, $C_8$-$C_{16}$, $C_{10}$-$C_{16}$, or $C_4$-$C_8$ alkylene, such as unsubstituted $C_6$-$C_{16}$, $C_6$-$C_{10}$, $C_8$-$C_{16}$, $C_{10}$-$C_{16}$, or $C_4$-$C_8$ alkylene. Preferably, $R^{18}$ and $R^{19}$ form a morpholino or imidazole.

In another preferred embodiment, $R^1$ is hydrogen; $R^2$, $R^3$, and $R^4$ are independently hydrogen, halogen, —OH, or —$OCH_3$; $R^5$ is hydrogen, —OH, or —$C(O)CH_3$; $R^6$ is $C_1$-$C_{12}$ alkylene; and $R^7$ is $N^+R^{18}R^{19}R^{20}$ ($Y^-$) wherein $R^{18}$ and $R^{19}$ are hydroxy substituted $C_1$-$C_{16}$ alkyl and $R^{20}$ is H.

In another preferred embodiment, $R^1$ is hydrogen; $R^2$, $R^3$, and $R^4$ are independently hydrogen, halogen, —OH, or —$OCH_3$; $R^5$ is hydrogen, —OH, or —$C(O)CH_3$; $R^6$ is $C_1$-$C_{12}$ alkylene; and $R^7$ is $N^+R^{18}R^{19}R^{20}$ ($Y^-$) wherein $R^{18}$ and $R^{19}$ are hydroxy substituted $C_1$-$C_{16}$ alkyl and $R^{20}$ is H.

In another preferred embodiment, $R^1$, $R^2$, $R^4$, $R^5$ are independently halogen or hydrogen; $R^3$ is —OH, or —$OCH_3$; and $R^7$ is $N^+R^{18}R^{19}R^{20}$ ($Y^-$) wherein $R^{18}$ and $R^{19}$ are hydroxy substituted $C_1$-$C_{16}$ alkyl and $R^{20}$ is H.

According to one preferred embodiment, $R^1$ is hydrogen; $R^2$, $R^3$, and $R^4$ are independently hydrogen, halogen, —OH, or —$OCH_3$; $R^5$ is hydrogen, —OH, or —$C(O)CH_3$; $R^6$ is $C_1$-$C_6$ alkylene or aryl substituted $C_1$-$C_{12}$ alkyl; and $R^7$ is —$NR^{18}R^{19}$ wherein $R^{18}$ and $R^{19}$ combine to form a 5, 6, or 7 membered heterocyclic ring or $N^+R^{18}R^{19}R^{20}$ ($Y^-$) wherein $R^{18}$ and $R^{19}$ are hydroxy substituted $C_1$-$C_{16}$ alkyl and $R^{20}$ is H.

In another preferred embodiment, the citrate salt of the compound is used.

Preferred delivery agent compounds include, but are not limited to those having the following formulae and salts thereof:

Compound 1

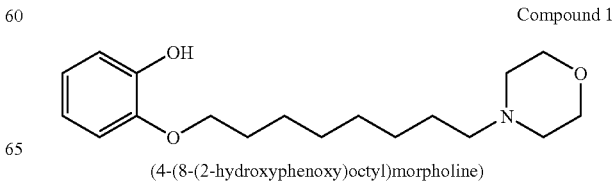

(4-(8-(2-hydroxyphenoxy)octyl)morpholine)

-continued

Compound 2

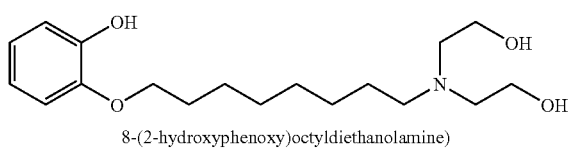

8-(2-hydroxyphenoxy)octyldiethanolamine)

Compound 3

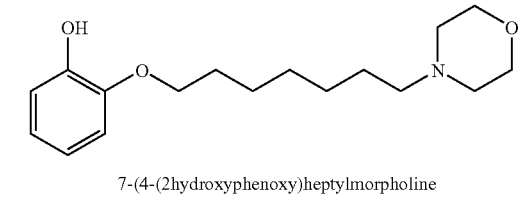

7-(4-(2hydroxyphenoxy)heptylmorpholine

Compound 4

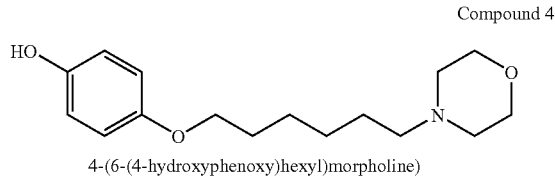

4-(6-(4-hydroxyphenoxy)hexyl)morpholine)

Compound 5

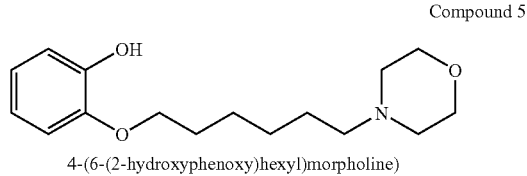

4-(6-(2-hydroxyphenoxy)hexyl)morpholine)

Compound 6

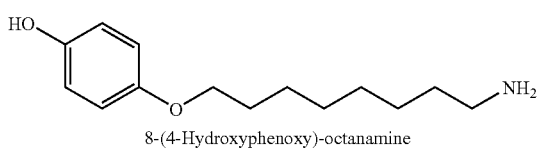

8-(4-Hydroxyphenoxy)-octanamine

Compound 7

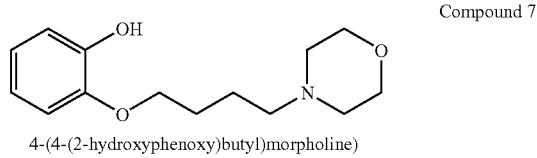

4-(4-(2-hydroxyphenoxy)butyl)morpholine)

Compound 8

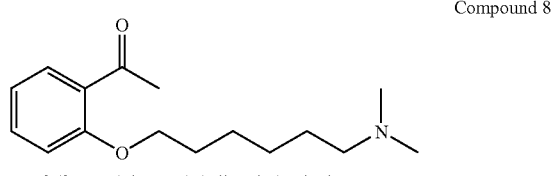

6-(2-acetylphenoxy)-1-dimethylaminohexane

Compound 9

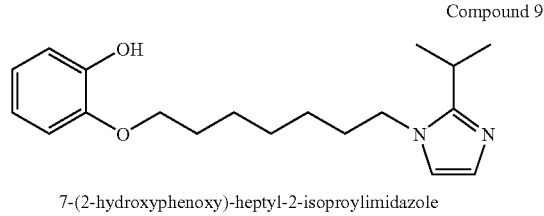

7-(2-hydroxyphenoxy)-heptyl-2-isoproylimidazole

-continued

Compound 10

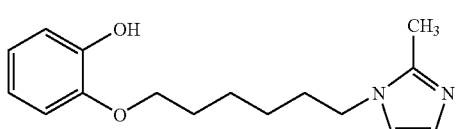

6-(2-hydroxyphenoxy)-hexyl-2-methylimidazole

Compound 11

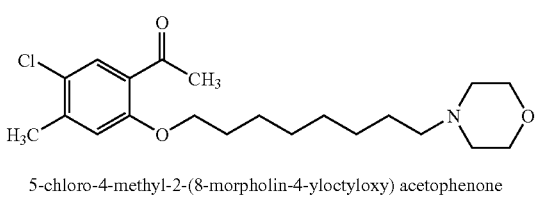

5-chloro-4-methyl-2-(8-morpholin-4-yloctyloxy) acetophenone

A preferred compound is the mesylate salt of compound 1.

Mixtures of these delivery agent compounds may also be used. Morpholine delivery agents of the present invention may be converted to morpholinium salts, which are also delivery agents, by methods known in the art.

The invention also provides a composition comprising at least one of the delivery agent compounds of the formulas above, and at least one active agent. These compositions deliver active agents to selected biological systems in increased or improved bioavailability of the active agent compared to administration of the active agent without the delivery agent compound.

Also provided are dosage unit forms comprising the compositions. The dosage unit may be in the form of a liquid or a solid, such as a tablet, capsule or particle, including a powder or sachet.

Another embodiment is a method for administering an active agent to an animal, particularly an animal in need of the active agent, by administering a composition comprising at least one of the delivery agent compounds of the formulas above and the active agent to the animal. Preferred routes of administration include the oral and intracolonic routes.

Yet another embodiment is a method of treating a disease or for achieving a desired physiological effect in an animal by administering the composition of the present invention.

Yet another embodiment is a method of preparing a composition of the present invention by mixing at least one delivery agent compound of the formulas above, and at least one active agent.

DETAILED DESCRIPTION OF THE INVENTION

Delivery Agent Compounds

The terms "alkyl", "alkenyl", and "alkynyl" as used herein include linear and branched alkyl, alkenyl, and alkynyl substituents, respectively.

The delivery agent compounds may be in the form of the free base or salts thereof. Suitable salts include, but are not limited to, organic and inorganic salts, for example ammonium, acetate salt, citrate salt, halide (preferably hydrochloride), hydroxide, sulfate, nitrate, phosphate, alkoxy, perchlorate, tetrafluoroborate, carboxylate, mesylate, fumerate, malonate, succinate, tartrate, acetate, gluconate, and maleate. Preferred salts include, but are not limited to, citrate and mesylate salts. The salts may also be solvates, including ethanol solvates, and hydrates.

Salts of the delivery agent compounds of the present invention may be prepared by methods known in the art. For example, citrate salts and mesylate salts may be prepared in ethanol, toluene and citric acid.

In general, the amine compounds of the present invention, i.e. where $R^7$ is —$NR^{18}R^{19}$, may be prepared by reacting the appropriate phenyl with either (1) the appropriate dihalogenated alkyl chain or (2) the appropriate haloalkylalcohol which can then be transformed into an appropriate leaving group, such as a methane sulfonic ester (e.g., by reaction with methanesulfonyl chloride), creating an ether compound with an active leaving group that is subsequently reacted with the appropriate amine optionally in the presence of a base, such as triethylamine. To obtain the corresponding salt the amine compound is reacted with the appropriate acid, i.e. to make the citric acid salt, the amine is reacted with citric acid and preferably with an excess of citric acid. To obtain the corresponding quaternary ammonium salt where $R^7$ is —$NR^{18}R^{19}R^{20}$ (where $R^{18}$, $R^{19}$, $R^{20}$ are not hydrogen), the amine moiety of the amine compound is alkylated by methods known in the art.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, acetonitrile, acetone, methanol, and tetrahydrofuran (THF) and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

The delivery agent may contain a polymer conjugated to it by a linkage group selected from the group consisting of —NHC(O)NH—, —C(O)NH—, —NHC(O), —OOC—, —COO—, —NHC(O)O—, —OC(O)NH—, —CH$_2$NH—NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly(propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastro-intestinal tract by acid hydrolysis, enzymes and the like. Also included as suitable active agents are those macromolecular agents whose physiochemical characteristics, such as, size, structure or charge, prohibit or impede absorption when dosed orally.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including α (e.g., interferon alfacon-1 (available as Infergen® from InterMune, Inc. of Brisbane, Calif.)), β and γ; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; anti-migraine agents such as BIBN-4096BS and other calcitonin gene-related proteins antagonists; glucagon-like peptide 1 (GLP-1); antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof.

Delivery Systems

The composition of the present invention comprises one or more delivery agent compounds of the present invention, and one or more active agents. In one embodiment, one or more of the delivery agent compounds, or salts of these compounds, or poly amino acids or peptides of which these compounds or salts form one or more of the units thereof, may be used as a delivery agent by mixing with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful for orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering the active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as those listed in the table below, in an animal by administering the composition of the present invention. Preferably, an effective amount of the composition for the treatment or prevention of the desired disease or for achieving the desired physiological effect is administered. Specific indications for active agents can be found in the Physicians' Desk Reference ($54^{th}$ Ed., 2000, Medical Economics Company, Inc., Montvale, N.J.), which is herein incorporated by reference. The active agents in the table below include their analogs, fragments, mimetics, and polyethylene glycol-modified derivatives.

| Active Agent | Disease and Physiological Effect |
| --- | --- |
| Growth hormones (including human recombinant growth hormone and growth-hormone releasing factors and its analogs) | Growth disorders |
| Interferons, including $\alpha$, $\beta$ and $\gamma$. | Viral infection, including chronic cancer and multiple sclerosis |
| Interleukin-1; interleukin-2. | Viral infection; cancer |
| Insulin; Insulin-like growth factor IGF-1. | Diabetes |
| Heparin | Thrombosis; prevention of blood coagulation |
| Calcitonin. | Osteoporosis; diseases of the bone |
| Erythropoietin | Anemia |
| Atrial naturetic factor | Vasodilation |
| Antigens | Infection |
| Monoclonal antibodies | To prevent graft rejection; cancer |
| Somatostatin | Bleeding ulcer; erosive gastritis |
| Protease inhibitors | AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; follicle stimulating hormone | Regulate reproductive function |

-continued

| Active Agent | Disease and Physiological Effect |
|---|---|
| Glucocerebrosidase | Gaucher disease (to metabolize lipoprotein) |
| Thrombopoietin | Thrombocytopenia |
| Filgrastim | Reduce infection in chemotherapy patients |
| Prostaglandins | Hypertension |
| Cyclosporin | Transplant rejection |
| Vasopressin | Bed-wetting; antidiuretic |
| Cromolyn sodium; Vancomycin | Asthma; allergies |
| Desferrioxamine (DFO) | Iron overload |
| Parathyroid hormone (PTH), including its fragments. | Osteoporosis; Diseases of the bone |
| Antimicrobials | Infection including gram-positive bacterial infection |
| Vitamins | Vitamin deficiencies |
| Bisphosphonates | Osteoporosis; Paget's disease; Inhibits osteoclasts |
| BIBN4096BS-(1-Piperidinecarboxamide. N-[2-[[5-amino-1-[[4-(4-pyridinyl)-1-piperazinyl)carbonyl]pentyl]amino]-1-[(3,5-dibromo-4-hydroxyphenyl)methyl]-2-oxoethyl]-4(1,4-dihydro-2-oxo-3(2H0-quinazolinyl)-.[R-(R*,S*)]-) | Anti-migraine; calcitonin gene-related peptide antagonist |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into the circulation. The bioavailability of the agent can be readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The following examples illustrate the invention without limitation. All parts are given by weight unless otherwise indicated.

Proton nuclear magnetic resonance ($^1$H NMR) analyses for the compounds listed below were conducted on a 300 MHz Bruker spectrometer using dimethyl sulfoxide (DMSO-$d_6$) as the solvent unless otherwise indicated.

Liquid chromatograph/mass spectrometry (LC-MS) analyses were performed with an Agilent Technologies, LC/MSD 1100 (single quad) having the following parameters:

Mobile Phase A: 50:950:5 acetonitrile:water:acetic acid (v/v/v)
Mobile Phase B: 950:50:5 acetonitrile:water:acetic acid (v/v/v)
Gradient Elution: 4 minute linear gradient 0-100% B; total time per injection is 11 minutes
Injection volume: 5 uL
Column: ZORBAX Rapid Resolution Cartridge, SB-C18, 2.1×30 mm, 3.5 um
Particle size, catalog # 873700-902
Column temp: 40° C.
UV detection at 244 nm MSD parameters:
Source: API-ES, positive polarity
Scan Parameters:
Mass Range: 125.00-600.00
Fragmentor: 60 V
Gain: 1.0 EMV
Threshold: 150
Spray Chamber:
Gas Temp. 350 deg. D
Drying Gas: 12.0 l/min
Neb. Pressure; 40 psig
VCap 4000V positive/negative.

EXAMPLE 1

Preparation of Compounds

1a: Preparation of Citrate Salt of Compound 1:

(4-(8-(2-hydroxyphenoxy)octyl)morpholine)citrate

A solution of 27.5 ml (31.4 grams, 157 mmol) of 2-benzyloxyphenyl, 80.0 ml (118.82 grams, 434 mmol) of 1,8-dibromooctane and 100 ml of ethanol was treated with 23.18 grams (168 mmol) of potassium carbonate and heated to reflux for 5.5 hours. The cooled reaction mixture was stirred for 20 hours at 25° C., filtered and concentrated. The residue was diluted with 100 ml of 2:1 hexanes/ethyl acetate and decolorized with charcoal. The solution was concentrated. This residue was purified by Kugelrohr distillation to remove the excess dibromide at 98° C. and 0.5 mm of pressure.

The 59.0 grams (151 mmol) of bromide isolated above was dissolved in 100 ml of tetrahydrofuran and treated with 28.0 ml (28.0 g, 321 mmol) of morpholine. This solution was heated to reflux for 4.5 hours. The resulting slurry was cooled to 25° C., stirred at 25° C. for 20 hours and treated with 80 ml of 2N aqueous sodium hydroxide. This mixture was diluted with 80 ml of 2:1 hexanes/ethyl acetate. The layers were separated. The organic phase was washed with water (3×30 ml) and brine (1×30 ml), dried over sodium sulfate, decolorized with charcoal and concentrated.

The 59.9 grams of benzyl ether isolated above was dissolved in 80 ml of ethanol and 20 ml of ethyl acetate, treated with 0.55 grams of 10% palladium on charcoal and placed under 58 psig of hydrogen in a Parr shaker. Approximately 20 psig of hydrogen was used up over 20 hours. The catalyst was removed by filtration through a Celite pad. The filtrate was concentrated and placed under vacuum over 20 hours.

The 4-8-(2-hydroxyphenoxy) octylmorpholine (37.63 grams, 122.4 mmol, about 80% pure by NMR) isolated above was dissolved in 50 ml of toluene and added to a warm solution of 21.17 g of citric acid and ethanol. Another 30 ml of toluene was added. The solution was placed in a −4° C. freezer. The solid that formed was isolated by filtration to give 42.9 g of 4-8-(2-hydroxyphenoxy) octylmorpholium citrate, mp 84-6° C. Karl Fisher: 0.55% water; Combustion analysis (with water): % C: 57.39 (calc'd), 57.63 (found); % H: 7.49 (calc'd), 7.55 (found); % N: 2.79 (calc'd), 2.64 (found); 1H NMR Analysis: (d6-DMSO): δ 8.4, bs, 5H; δ 6.9, dd, 1H; δ 6.7, m, 3H; δ 3.9, t, 2H; δ 3.7, t, 4H; δ 2.8, bt, 4H; δ 2.7, t, 2H; δ 2.6, q, 4H; δ 1.7, p, 2H; δ 1.5, p, 2H; δ 1.4, p, 2H; δ 1.3, m, 6H.

1b: Preparation of Mesylate Salt of Compound 1:

(4-(8-(2-hydroxyphenoxy)octyl)morpholine)mesylate

The N-8-(2-hydroxyphenoxy)octylmorpholine (13.3 g, 43.3 mmol, about 80% pure by NMR) isolated above was dissolved in 40 ml of tetrahydrofuran and treated with 2.30 ml (3.41 g, 35.4 mmol) of methanesulfonic acid. A solid immediately developed and was isolated by filtration to give 8.02 g of compound 1 as the mesyalte salt, mp 137-9 C. Combustion analysis: % C: 56.55 (calc'd), 56.50 (found); % H: 8.24 (calc'd), 8.23 (found); % N: 3.47 (calc'd), 3.39 (found); % S: 7.94 (calc'd), 7.79 (found); 1H NMR Analysis: (d6-DMSO): $\delta$ 9.6, bs, 1H; $\delta$ 8.8, bs, 1H; $\delta$ 6.9, dd, 1H; $\delta$ 6.7, m, 3H; $\delta$ 3.9, t, 4H; $\delta$ 3.7, t, 2H; $\delta$ 3.4, t, 2H; $\delta$ 3.0, bt, 4H; $\delta$ 2.4, s, 3H; $\delta$ 1.7, m, 4H; $\delta$ 1.4, p, 2H; $\delta$ 1.3, m, 6H.

1c. Preparation of Compound 3:

7-(4-(2hydroxyphenoxy) heptylmorpholinium citrate

May be made in the same manner as compound 1 using 1,7-dibromohexane as the alkylating agent. 2.25 g of compound 3 was isolated, mp 120-3 C. Combustion analysis: % C: 56.90 (calc'd), 56.92 (found); % H: 7.27 (calc'd), 7.24 (found); % N: 2.88 (calc'd), 2.61 (found); 1H NMR Analysis: (d6-DMSO): $\delta$ 8.6, bs, 5H; $\delta$ 6.9, dd, 1H; $\delta$ 6.7, m, 3H; $\delta$ 3.9, t, 2H; $\delta$ 3.7, t, 4H; $\delta$ 2.8, bt, 4H; $\delta$ 2.7, t, 2H; $\delta$ 2.6, q, 4H; $\delta$ 1.7, p, 2H; $\delta$ 1.5, p, 2H; $\delta$ 1.2-1.4, m, 6H.

1d: Preparation of Citrate Salt of Compound 2:

8-(2-hydroxyphenoxy) octyldiethanolamine) citrate

A solution of 27.5 ml (31.4 g, 157 mmol) of 2-benzyloxyphenyl, 80.0 ml (118.82 g, 434 mmol) of 1,8-dibromooctane and 100 ml of ethanol was treated with 23.18 g (168 mmol) of potassium carbonate and heated to reflux for 5.5 hours. The cooled reaction mixture was stirred for 20 hours at 25° C., filtered and concentrated. The residue was diluted with 100 ml of 2:1 hexanes/ethyl acetate and decolorized with charcoal. The solution was concentrated. This residue was purified by Kugelrohr distillation to remove the excess dibromide at 980 C and 0.5 mm of pressure.

The bromide isolated above (4.32 g, 11.0 mmol) and 2.80 ml (3.07 g, 29.2 mmol) of diethanolamine were dissolved in 30 ml of tetrahydrofuran and treated with 5 mL of triethylamine. This solution was heated to reflux for 3 days. The resulting slurry was cooled to 25° C., stirred at 25° C. for 20 hours and treated with 20 ml of 2N aqueous sodium hydroxide. This mixture was diluted with 20 ml of ethyl acetate. The layers were separated. The organic phase was washed with water (3×30 ml) and brine (1×30 ml), dried over sodium sulfate, and concentrated.

The 3.98 g of benzyl ether isolated above was dissolved in 20 ml of ethanol and 20 ml of ethyl acetate, treated with 0.22 g of 10% palladium on charcoal and placed under 58 psig of hydrogen in a Parr shaker. Approximately 20 psig of hydrogen was used up over 20 hours. The catalyst was removed by filtration through a Celite pad. The filtrate was concentrated and placed under vacuum over 20 hours.

The 8-(2-hydroxyphenoxy)octyldiethanolamine (3.06 g, 9.40 mmol) isolated above was dissolved in 10 ml of methyl t-butyl ether and 2 ml ethanol. This solution was added to a warm solution of 1.82 g of citric acid and 8 ml ethanol. Another 5 ml of methyl t-butyl ether was added. The solution was placed in a −4° C. freezer. The solid that formed was isolated by filtration to give 2.16 g of 8-(2-hydroxyphenoxy) octyldiethanolammonium citrate, mp<25° C. Karl Fisher: 0.1.71% water; Combustion analysis (with water): % C: 54.74 (calc'd), 55.28 (found); % H: 7.66 (calc'd), 8.16 (found); % N: 2.66 (calc'd), 2.54 (found).

1e: Preparation of Citrate Salt of Compound 4:

4-(6-(4-hydroxyphenoxy)hexyl)morpholine)citrate

A solution of 9.97 g (49.8 mmol) of 4-benzyloxyphenyl, 22.2 ml (34.9 g, 143 mmol) of 1,6-dibromohexane and 100 ml of ethanol was treated with 7.67 g (55.5 mmol) of potassium carbonate and heated to reflux for 5.5 hours. The reaction mixture was cooled to 25° C. At 25° C. the solidified reaction mixture was diluted with ethyl acetate and ethanol, filtered, and rinsed with copious amounts of ethyl acetate. The filtrate was collected and concentrated to form a solid. The solid was isolated by filtration.

The 4.20 g (11.6 mmol) of bromide isolated above was dissolved in 30 ml of tetrahydrofuran and treated with 2.20 ml (2.20 g, 25.3 mmol) of morpholine. This solution was heated to reflux for 4.5 hours. The resulting slurry was cooled to 25° C., stirred at 25°C. for 20 hours and treated with 20 ml of 2N aqueous sodium hydroxide. This mixture was diluted with 20 ml of 2:1 hexanes/ethyl acetate. The layers were separated. The organic phase was washed with water (3×30 ml) and brine (1×30 ml), dried over sodium sulfate, decolorized with charcoal and concentrated.

The 4.27 g of benzyl ether isolated above was dissolved in 25 ml of ethanol and 20 ml of ethyl acetate, treated with 0.32 g of 10% palladium on charcoal and placed under 58 psig of hydrogen in a Parr shaker. Approximately 20 psig of hydrogen was used up over 20 hours. The catalyst was removed by filtration through a Celite pad. The filtrate was concentrated and placed under vacuum for over 20 hours.

The 4-6-(4-hydroxyphenoxy) hexylmorpholine (3.05 g, 10.9 mmol) isolated above was dissolved in 60 ml of ethanol, 20 ml of ethyl acetate and 20 ml of acetone with heating. This solution was added to a warm solution of 2.10 g of citric acid and ethanol. The mixture was diluted with 50 ml of methyl t-butyl ether and placed in a −4° C. freezer. The solid that formed was isolated by filtration to give 2.16 g of 4-6-(4-hydroxyphenoxy) hexylmorpholinium citrate, mp 125-7° C. Karl Fisher: 0.45% water; Combustion analysis (with water): % C: 55.79 (calc'd), 55.47 (found); % H: 7.07 (calc'd), 7.03 (found); % N: 2.96 (calc'd), 2.92 (found).

1f. Preparation of Citrate Salt of Compound 5:

4-(6-(2-hydroxyphenoxy)hexyl)morpholinium citrate

Preparation is the same as for compound 1 citrate except 1,6-dibromohexane was used as the alkylating agent. 10.11 g of compound 5 was isolated, mp 76-80 C. Combustion analysis: % C: 55.70 (calc'd), 56.11 (found); % H: 7.08 (calc'd), 7.22 (found); % N: 2.95 (calc'd), 2.86 (found); 1H NMR Analysis: (d6-DMSO): $\delta$ 8.6, bs, 5H; $\delta$ 6.9, dd, 1H; $\delta$ 6.7, m, 3H; $\delta$ 3.9, t, 2H; $\delta$ 3.7, t, 4H; $\delta$ 2.8, bt, 4H; $\delta$ 2.7, t, 2H; $\delta$ 2.6, q, 4H; $\delta$ 1.7, p, 2H; $\delta$ 1.5, p, 2H; $\delta$ 1.4, p, 2H; $\delta$ 1.3, p, 2H.

1 g. Preparation of Compound 6:

8-(4-hydroxyphenoxy)octanamine

A mixture of 4-benzyloxyphenyl (10.23 grams, 51.2 mmol) and ethyl 8-bromooctanoate (12.80 grams, 51.0 mmol) in 200 ml of 2-butanone was treated with 13.8 grams of potassium carbonate (100 mmol) and heated to reflux for 16 hours. The cooled reaction mixture was filtered. The filtrate was combined with 100 ml of ethyl acetate and washed in sequence with 2N NaOH, water, 1N HCl and brine, dried over anhydrous sodium sulfate. Solvent was removed by rotary evaporator to give a white solid as the product.

The 18.53 grams (50.1 mmol) of the ester obtained above was dissolved in 200 ml of anhydrous tetrahydrofuran. Lithium aluminum hydride (1.9 grams, 50 mmol) was added slowly through a powder funnel. This mixture was stirred at room temperature for 2 hours before cooled in an ice bath. Water (2 ml) was added slowly followed by 6 ml of 15% NaOH and then another 2 ml of water. The mixture was stirred overnight before filtration. The filtrate was concentrated to give 16.3 grams of product.

The 16.3 grams (49.7 mmol) of alcohol obtained above was dissolved in a mixture of 200 ml of methylene chloride and 10 ml of N,N-dimethylacetamide. Triethylamine (7.30 grams, 72.3 mmol) was added. The resulting mixture was cooled in an ice-bath before methanesulfonyl chloride (7.39 grams, 64.5 mmol) was added. The mixture was then warmed to room temperature and stirred for 20 hours. The mixture was then washed in sequence with water, 1N HCl, water, saturated sodium bicarbonate, water and brine, dried over sodium sulfate. Evaporation of the solvent afforded 21.25 grams of product.

The mesylate (20.50 grams, 50.5 mmol) obtained above was dissolved in 100 ml of N,N-dimethylacetamide and treated with sodium azide (5.01 grams, 77.1 mmol). The mixture was heated at 120° C. for three hours before cooled to room temperature. The mixture was then poured into 200 ml water, and the large amount of the solid formed was collected by vacuum filtration (17.25 grams).

The azide (16.64 grams, 47.1 mmol) obtained above was dissolved in 200 isopropanol and treated with ammonium formate (11.87 grams, 188.4 mmol). The mixture was heated to 60° C. before palladium on carbon (10% in weight, 1.0 grams) was added slowly through a powder funnel. The reaction was stirred at 60° C. for one hour before cooled to room temperature. Solvent was removed by rotary evaporation to obtain 13.09 grams of solids. The solid was recrystallized from ethanol-water to afford 8.90 grams of pure product of 8-(4-hydroxyphenoxy)octanamine, mp 115-7° C. % C: 70.85 (calc'd), 70.53 (found); % H: 9.77 (calc'd), 9.92 (found); % N: 5.90 (calc'd), 5.67 (found); 1H NMR Analysis: (d6-DMSO): δ 6.7, AB, 4H; δ 3.8, t, 2H; δ 3.5, bt, 3H; δ 2.5, t, 2H; δ 1.6, p, 2H; δ 1.3, br, 10H.

1 h. Preparation of Citrate Salt of Compound 7:

4-(4-(2-hydroxyphenoxy)butyl)morpholinium Citrate

Preparation is the same as the compound 1 citrate except used 1,4-dibromobutane as the alkylating agent. 6.32 g of compound 7 was isolated, mp 97-9 C. Combustion analysis: % C: 54.17 (calc'd), 54.11 (found); % H: 6.59 (calc'd), 6.61 (found); % N: 3.16 (calc'd), 3.08 (found); 1H NMR Analysis: (d6-DMSO): δ 6.9, dd, 1H; δ 6.7, m, 3H; δ 4.0, t, 2H; δ 3.7, t, 4H; δ 2.8, bt, 4H; δ 2.7, t, 2H; δ 2.6, q, 4H; δ 1.7, m, 4H.

1i: Preparation of Hydrochloride Salt of Compound 8:

6-(2-acetylphenoxy)-1-dimethylaminohexane hydrochloride

A solution of 9.32 g (68.5 mmol) of 2-hydroxyacetophenone, 11.3 mL (9.94 g, 68.5 mmol) of 6-dimethylamino-1-hexanol, and 18.00 g (68.6 mmol) of triphenylphosphine in 70 mL of tetrahydrofuran (THF) was prepared. A solution of 13.5 mL (13.86 g, 68.6 mmol) of diisopropyl azodicarboxylate (DIAD) in 30 mL of THF was added to the above solution over approximately 30 minutes. The reaction mixture was stirred at ambient temperature for 20 hours, diluted with 100 mL of ethyl acetate and extracted with five 50 mL portions of 1% aqueous hydrochloric acid and two 30 mL portions of 10% aqueous hydrochloric acid. The combined aqueous extracts were brought to pH=9.5 by the addition of 10 N sodium hydroxide, and extracted with three 50 mL portions of ethyl acetate. The combined organic phase was dried over sodium sulfate and concentrated in vacuo. The resulting slurry was diluted with 10 mL of ethyl acetate and the solids removed by filtration through glass wool. The organic phase was concentrated in vacuo and refrigerated. The resulting solids were diluted with approximately 40 mL of 10% aqueous hydrochloric acid, and the insoluble fraction removed by filtration. The solution was brought to pH=9 with 1 N sodium hydroxide, washed with four 30 mL portions of ethyl acetate and one 30 mL portion of water, dried over sodium sulfate, concentrated in vacuo, and stored at −5° C. The resulting solids were stirred in hexanes, and the insoluble fraction removed by filtration. Gaseous hydrochloric acid was bubbled through the filtrate. The hexanes were decanted off the resulting solids, and the solids were stirred in ethyl acetate for approximately 20 hours. These solids were collected by filtration to give 5.77 g (28.1%) of 6-(2-acetylphenoxy)-1-dimethylaminohexane hydrochloride as a pale yellow powder. Melting point 138-141° C. Combustion analysis: % C: 64.09 (calc'd), 63.80 (found); % H: 8.74 (calc'd), 8.60 (found); % N: 4.67 (calc'd), 4.76 (found); % Cl: 11.82 (calc'd), 11.63 (found). 1H NMR Analysis (d6-DMSO): δ 10.8, bs, 1H; δ 7.6, dd, 1H; δ 7.5, dt, 1H; δ 7.1, d, 1H; δ 7.0, dt, 1H; δ 4.1, t, 2H; δ 3.0, m, 2H; δ 2.7, d, 6H; δ 2.5, s, 3H; δ 1.8, m, 2H; δ 1.7, m, 2H; δ 1.5, m, 2H, δ 1.4, m, 2H.

1j. Preparation of Compound 9

The 7-bromoheptyl 2-benzyloxyphenyl ether may be prepared in the same manner as above from 2-benzyloxyphenyl and 1,7-dibromoheptane. A suspension of 16.49 g (149.7 mmol) of 2-isopropylimidazole, 28.80 g (76.33 mmol) of 7-bromoheptyl 2-benzyloxyphenyl, 11.2 ml of triethylamine and 150 ml of dioxane was heated to 80C, causing all the solids to go into solution. After stirring for 5 hr, the reaction mixture was cooled to 25C, diluted with 50 n ml of methyl t-butyl ether and filtered. The filtrate was diluted with 2:1 methyl t-butyl ether and hexanes and washed with water (3×60 mL) and brine (1×40 mL). The organic phase (the top one) was dried over sodium sulfate concentrated.

The crude 31.0 g of benzyl ether isolated above was dissolved in ethanol and cooled to −4C. The solid that formed was isolated and discarded. The filtrate was concentrated to half the volume (150 mL), treated with 0.50 g of 10% palladium on charcoal and placed under 53 psig of hydrogen in a Parr shaker. Approximately 4 psig of hydrogen was used up over 40 hours. The catalyst was removed by filtration through a Celite pad. The filtrate was concentrated. After 2 days, a solid formed, was taken up in toluene, filtered off and recrystallized from ethanol/toluene. This solid was subjected to Kugelrohr distillation to remove the 2-isopropylimidazole impurity at 66C and 0.1 mm. Upon cooling 5.89 g of (2-hydroxyphenoxy)-heptyl-2-isoproylaimidazole was isolated, mp 93-4C. Karl Fisher: 1.66% water; Combustion analysis (with water): %C: 70.92 (calc'd), 70.20 (found); %H: 8.96 (calc'd), 8.80 (found); % N: 8.71 (calc'd), 8.52 (found); MS (M+1) 317; 1H NMR Analysis: (d6-DMSO): δ 8.8, bs, 1H; b 7.05, d, 1H; δ 6.9, dd, 1H; δ 6.8, d, 1H; δ 6.7, m, 3H; δ 3.9, m, 4H; δ 3.05, hept, 1H; δ 1.7, m, 4H; δ 1.3-1.5, m, 6H; δ 1.2, d, 6H.

1 k. Preparation of Compound 10

The compound may be made by the same procedure as for compound 9 using 1,6-dibromohexane as the alkylating agent and 2-methyl-imidazole. A total of 2.11 g of compound 10 was isolated, mp 103-4C. Combustion analysis: %C: 70.04 (calc'd), 70.24 (found); %H: 8.08 (calc'd), 8.29 (found); %N: 10.21 (calc'd), 9.97 (found); 1H NMR Analysis: (d6-DMSO): δ 8.8, bs, 1H; δ 7.0, d, 1H; δ 6.9, dd, 1H; δ 6.8, m, 3H; δ 6.7, d, 1H; δ 3.9, t, 2H; δ 3.85, t, 2H; δ 1.7, m, 4H; δ1.45, p, 2H; δ 1.3, p, 2H.

1l. Preparation of Compound 11

A solution of 10.0 g (47.8 mmol) of 8-bromo-1-octanol, 10.41 g (120 mmol) of morpholine and tetrahydrofuran was heated to reflux for 3 hr. The cooled reaction mixture was treated with saturated aqueous sodium bicarbonate and extracted with ethyl acetate. The organic phase was washed with brine, dried over magnesium sulfate and concentrated to give 10.50 g of 4-(8-hydroxyoctyl)morpholine.

The crude 4-(8-hydroxyoctyl)-morpholine (2.0 g, 9.3 mmol) was dissolved in methylene chloride and treated with 10 ml of triethylamine (7.3 g, 72 mmol). After cooling in an ice bath, the mixture was treated with 1.28 g (11.2 mmol) of methanesulfonyl chloride stirring for 1 hr before warming to 25C. After stirring for 2 hour, the reaction mixture was diluted with aqueous sodium bicarbonate solution and extracted with ethyl acetate. The organic phase was washed with brine, dried over magnesium sulfate and concentrated to give 2.4 g of crude mesylate.

A solution of 2.40 g (8.2 mmol) of crude 8-morpholinooctyl mesylate, 1.82 g (9.8 mmol) of 2-hydroxy-5-chloro-4-methylacetophenone and 30 ml of dimethylformamide was treated with 2.26 g (16.4 mmol) of potassium carbonate and 0.62 g (4.1 mmol) of sodium iodide. The reaction mixture was heated. After workup and treatment with 1.0 M hydrogen chloride in ethyl ether, 2.67 g of 5-chloro-4-methyl-2-(8-morpholin-4-yloctyloxy)acetophenone hydrochloride was isolated, mp 75-6C. Karl Fisher: 4.89% water; Combustion analysis: %C: 57.34 (calc'd), 56.42 (found); %H: 8.11 (calc'd), 8.3 (found); %N: 3.18 (calc'd), 3.81 (found); %Cl: 16.12 (calc'd), 16.72 (found); 1H NMR Analysis: (d6-DMSO): δ 11.0, bs, 1H; δ 7.55, s, 1H; δ 7.2, s, 1H; δ 4.1, t, 2H; δ 3.9, m, 2H; δ 3.8, t, 2H; δ 3.0, m, 4H; δ2.5, s, 3H; δ 2.5, m, 2H; δ 2.4, s, 3H; δ 1.8, p, 2H; δ 1.7, m, 2H; δ 1.45, m, 2H; δ 1.3, m, 6H.

EXAMPLE 2

2A: Insulin—Oral Delivery

Oral dosing (PO) compositions of delivery agent compound and human zinc insulin (minimum 26 IU/mg available from Calbiochem-Novabiochem Corp, La Jolla, Calif.) were prepared in deionized water. Typically, 500 mg of delivery agent compound was added to 1.5 ml of water. The solution was vortexed, then heated (about 37° C.) and sonicated. The pH was adjusted to about 7 to 8.5 with NaOH or HCl. Additional NaOH was added, if necessary, to achieve uniform solubility, and the pH re-adjusted to about 7 to 8.5. Water was then added to bring the total volume to about 2.4 ml and vortexed. About 1.25 mg insulin from an insulin stock solution (15 mg/ml made from 0.5409 g insulin and 18 ml deionized water, adjusting with HCl and NaOH to pH 8.15 and to obtain a clear solution using 40 ml concentrated HCl, 25 ml 10N NaOH and 50 ml 1N NaOH) was added to the solution and mixed by inverting. The solution may be used in the dosing protocol immediately, or alternatively, the solution may be placed into a 37° C. water bath for one hour prior to dosing. The final delivery agent compound dose, insulin dose and dose volume amounts are listed below in Table 1.

The typical dosing and sampling protocols were as follows. Male Sprague-Dawley rats weighing between about 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=15, 30, 60, 120 and 180 minutes. The percent change in glucose levels from baseline is reported in Table 1.

TABLE 1

Insulin - Oral Delivery

| Delivery Agent Compound | Delivery Agent Compound Dose (mg/kg) | Insulin Dose (mg/kg) | Volume dose (ml/kg) | Glucose Levels in Serum (% change from baseline ± SD) |
|---|---|---|---|---|
| 1 | 200 | 0.5 | 2 | 0.3 ± 8.2 |
| 1 | 200 | 0.5 | 2 | −5.9 ± 4.6 |
| 2 | 200 | 0.5 | 2 | −10.8 ± 6.8 |
| 3 | 200 | 0.5 | 2 | −9.8 ± 4 |
| 4 | 200 | 0.5 | 2 | −2.3 ± 10.6 |
| 6 | 200 | 0.5 | 2 | 6.4 ± 17.1 |
| 7 | 200 | 0.5 | 2 | −11.7 ± 3.4 |
| 8 | 200 | 0.5 | 2 | −8.2 ± 9.5 |

The aforementioned procedure was repeated with the following modifications:

Male Sprague-Dawley rats weighing from 250 to 300 g were used rather than rats weighing between 200 and 250 g. All animals were stored in wire cages. All animals were placed in the room in which the experiment was performed at least 30 minutes before the experiment. All loud noises and voices were avoided to reduce stress to the animals.

Test strips used to determine the level of glucose in blood samples were only exposed to light as needed. All test strips were stored individually in closed vials except during use.

When running a control, the control solution was vigorously shaken, the first drop was discarded, the bottle tip was wiped off with a kim wipe, and one drop was applied to a test strip.

Blood samples were taken at t=0, 15, 30, 45, and 60 minutes by the Farmer's Wife Technique. Each rat's tail was cut at tip (about 2 mm of the tail). The first drop of blood from the animal's tail was not used to take a blood glucose reading. A fresh drop of blood from the tip of each rat's tail was placed on the tip of a test strip.

After baselines, the animals were orally dosed while fully conscience. No anesthesia was given.

2B: Biotinylated Ribonuclease A (bRNase A) Oral Delivery

Oral gavage (PO) dosing solutions of delivery agent compound and bRNase A (Sigma (Milwaukee, Wis.): Ribonuclease A Type XII-A from bovine pancreas) in deionized water is prepared by mixing. A solution of the delivery agent compound is made. The delivery agent compound solution is prepared in phosphate buffer and stirred. If necessary, the pH of the mixture is adjusted upwards by the addition of aliquots of NaOH of an appropriate normality until the delivery agent compound is completely dissolved. The final pH of the dissolved delivery agent compound is between 7.5 and 9.5. The final dosing solutions are prepared by mixing 9 volumes of the delivery agent compound solution with 1 volume of a bRNase A stock solution (20 mg bRNase A in phosphate buffered saline (PBS)). Final concentrations are 150 mg/ml delivery agent compound and 2 mg/ml bRNase A.

The dosing and sampling protocols are as follows. Male Sprague-Dawley rats weighing 200-250 g are fasted for 24 hours and administered ketamine (44 mg/kg) and chlorpromazine (1.5 mg/kg) 15 minutes prior to dosing and again as needed to maintain anesthesia. A dosing group of five animals is administered one of the dosing solutions in the following manner. An 11 cm Rusch 8 French catheter is adapted to a 1 ml syringe with a pipette tip. The syringe is filled with dosing solution by drawing the solution through the catheter, which is then wiped dry. The catheter is placed down the esophagus leaving 1 cm of tubing past the incisors. The dosing solution is administered by pressing the syringe plunger. Blood samples are collected serially from the tail artery at 15, 30, 45, 60 and 90 minutes. Serum bRNase A concentrations are quantified by a modified immunoassay as described below.

Biotinylation of Ribonuclease A

To label each of the RNase A molecules with one biotin molecule, the ratio of the activated biotin is maintained at 3 moles biotin/1 mole RNase A. In a representative biotinylation reaction 500 mg of RNase A is dissolved in 20 ml of 50 mM $NaHCO_3$, pH 7.6. 57.08 mg of EZ-Link Sulfo-NHS-LC-LC Biotin (Pierce Chemical Company, Rockford, Ill.) is added to the solution, dissolved and allowed to stand on ice for 2 hours. The reaction mix is then dialyzed (10,000 MW cutoff dialysis membrane (Pierce, Rockford, Ill.)) against 4 liters of PBS at 4° C. overnight. The reaction mixture is placed in 4 liters of fresh PBS and dialyzed for an additional 4 hours. The dialyzed bRNase A is removed from the dialysis membrane, diluted to a final volume of 25 ml with PBS (final concentration of bRNase A=20 mg/ml), and stored a 4° C.

Assay of Serum Levels of Orally Administered bRNase A

In general 100 µl aliquots of the rat sera collected at the various time points are placed in the appropriate wells of a 96 well Reacti-Bind Streptavidin Coated Polystyrene Plates (Pierce). After a 2 hour incubation period the plates are washed and then incubated with a polyclonal rabbit anti-RNase A (Chemicon, Pittsburgh, Pa.). After washing, the plates are incubated for 2 hours with a polyclonal goat anti-rabbit IgG (Chemicon, Pittsburgh, Pa.) conjugated to alkaline phosphatase. The plates are washed after the incubation and the amount of initially captured bRNase A is detected by the addition of para-nitrophenyl phosphate (a substrate for alkaline phosphatase) (Pierce, Rockford, Ill.). The amount of bRNase A circulating in the original rat sera is quantitated by comparison with a standard curve of bRNAse A which extends from 1000-0.1 ng/mL in fifteen two-fold dilutions. The maximum±standard deviation is given in Table 2 below.

TABLE 2

Oral Delivery of RNAase

| Delivery Agent Compound | Delivery Agent Compound Dose (mg/kg) | bRNAase Dose (mg/kg) | Volume dose (ml/kg) | Mean Peak Serum ng/ml |
|---|---|---|---|---|

2c: Oral Delivery of BIBN4096BS

Oral gavage (PO) dosing solutions of delivery agent compound and the calcitonin gene-related peptide antagonist, 1-piperidinecarboxamide, N-[2-[[5-amino-1-[[4-(4-pyridinyl)-1-piperazinyl)carbonyl]pentyl]amino]-1-[(3,5-dibromo-4-hydroxyphenyl)methyl]-2-oxoethyl]-4(1,4-dihydro-2-oxo-3(2H0-quinazolinyl)-. [R—(R*,S*)]- (BIBN4096BS) in water were prepared. Typically, a solution of the delivery agent compound was prepared in water and stirred. The final dosing solutions were prepared by mixing the delivery agent compound with a BIBN4096BS stock solution and diluting to the desired volume (usually 1.0 mL). If necessary, the pH of the mixture was adjusted by the addition of aliquots of aqueous hydrochloric acid solution of an appropriate normality until the final pH of the dissolved delivery agent compound was below 7.0. The final compound amounts per dose were 25 mg/kg of BIBN4096BS and 200 mg/kg of delivery agent compound in a total volume of 1 mL/kg.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger. Blood samples were collected serially from the tail artery, typically at time=0, 15, 30, 45, and 60 minutes for oral. Plasma BIBN4096BS concentrations were quantified by using a liquid chromatography/mass spectrometry/mass spectrometry assay method using UV detection. The standard range for the assay was 5-2,000 ng/mL. Previous studies indicated baseline values of about 10 ng/mL. The maximum is reported below in Table 3.

TABLE 3

Oral BIBN4096BS Delivery

| Delivery Agent Compound | Delivery Agent Compound Dose (mg/kg) | BIBN4096BS Dose (mg/kg) | Volume dose (ml/kg) | Mean Peak Serum ± sd ng/ml |
|---|---|---|---|---|
| 1 (Citrate) | 200 | 25 | 1 | 540 ± 521 |
| 1 (Citrate) | 200 | 25 | 1 | 148 ± 119 |
| 1 (Citrate) | 200 | 25 | 1 | 117 ± 76 |
| 1 (Citrate) | 200 | 25 | 1 | 277 ± 332 |
| 1 (Citrate) | 200 | 25 | 1 | 66 ± 7 |
| 1 (Citrate) | 200 | 25 | 1 | 153 ± 158 |
| 1 (Mesylate) | 200 | 25 | 1 | 408 ± 340 |

TABLE 3-continued

Oral BIBN4096BS Delivery

| Delivery Agent Compound | Delivery Agent Compound Dose (mg/kg) | BIBN4096BS Dose (mg/kg) | Volume dose (ml/kg) | Mean Peak Serum ± sd ng/ml |
|---|---|---|---|---|
| 1 (Mesylate) | 200 | 25 | 1 | 608 ± 552 |
| 2 | 200 | 25 | 1 | 428 ± 340 |
| 2 | 200 | 25 | 1 | 352 ± 248 |
| 2 | 200 | 25 | 1 | 416 ± 438 |
| 2 | 200 | 25 | 1 | 756 ± 381 |
| 3 | 200 | 25 | 1 | 166 ± 159 |
| 3 | 200 | 25 | 1 | 451 + 156 |
| 3 | 200 | 25 | 1 | 139 ± 150 |
| 3 | 200 | 25 | 1 | 131 ± 114 |
| 4 | 200 | 25 | 1 | 70 ± 39 |
| 4 | 200 | 25 | 1 | 59 ± 26 |
| 6 | 200 | 25 | 1 | 35 ± 32 |
| 6 | 200 | 25 | 1 | 77 ± 35 |
| 6 | 200 | 25 | 1 | 69 ± 61 |
| 7 | 200 | 25 | 1 | 48 ± 49 |
| 7 | 200 | 25 | 1 | 12 ± 10 |
| 8 | 200 | 25 | 1 | 59 ± 35 |
| 8 | 200 | 25 | 1 | 115 ± 110 |
| 8 | 200 | 25 | 1 | 93 ± 105 |
| 8 | 200 | 25 | 1 | 79 ± 32 |

2d. Oral Delivery of Daptomycin

2d. Daptomycin—Oral/Intracolonic Delivery

Dosing solutions containing a delivery agent compound and daptomycin (Cubist Pharmaceuticals, Cambridge, Mass.) were prepared in 0.9% normal saline. A solution of the compound was made either with the sodium salt of the compound or by converting the free acid to its sodium salt. The free acid of the delivery agent compound was converted to the sodium salt with one equivalent of sodium hydroxide. This mixture was vortexed and placed in a sonicator (about 37° C.). The pH was adjusted to about 7.0-7.5 with aqueous HCl or NaOH. Additional NaOH was added, if necessary, to achieve uniform solubility, and the pH readjusted. The mixture was vortexed to produce a uniform solution, also using sonication if necessary. The delivery agent compound solution was mixed with daptomycin from a stock solution (200 mg daptomycin/mL in 0.9% normal saline and the pH adjusted, if necessary, to between 6.0-7.0 with NaOH or HCl). The stock solution was stored frozen (−20° C.) wrapped in foil, then thawed and warmed gradually to about 25° C. before using. The delivery agent-daptomycin mixture was vortexed at low speed to produce a uniform solution. The pH was adjusted to about 7.0-7.5 with aqueous NaOH. The solution was then diluted with 0.9% normal saline to the desired volume (usually 2.0 ml) and concentration and stored wrapped in foil before use. The final delivery agent compound and daptomycin doses, and the dose volumes are listed below in Table 4.

The typical dosing and sampling protocols were as follows. Male Sprague-Dawley rats weighing between 200-250 g were fasted for 24 hours and were anesthetized with ketamine (44 mg/kg) and thorazine (1.5 mg/kg) 15 minutes prior to dosing and again as needed to maintain anesthesia. A dosing group of five animals was administered one of the dosing solutions. For oral gavage (PO) dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger. For intracolonic (IC) dosing, a 7.5 cm, 8 fr Rusch catheter was adapted to a 1 ml syringe with a pipette tip. The dosing catheter was inserted into the colon through the anus until the tube was no longer visible. The dosing solution was expressed slowly into the colon by pressing the syringe plunger.

Heparinized rat blood samples were collected via the ventral tail artery, typically at 0.25, 0.5, 0.75, 1.0, 2.0, and 4.0 hours after dosing, and stored on ice. Blood samples were then spun (centrifuged) at 11,500 rpm for 4 minutes at 4° C. to obtain the plasma (supernatant), which was stored at −70° C. The plasma daptomycin concentrations were measured by isocratic reversed phase HPLC, keeping samples at 4° C. during analysis. Blank plasma studies show baseline values of zero.

Results from the animals in each group were averaged for each time point and the highest of these averages (i.e., mean peak daptomycin concentration, $C_{max}$) is reported below in Table 4.

TABLE 4

Daptomycin - Oral/Intracolonic Delivery

| Delivery Agent Compound | Route of dosing | Delivery Agent Compound Dose (mg/kg) | Daptomycin Dose (mg/kg) | Volume dose (mL/kg) | Mean plasma Cmax [daptomycin] ± SD, µg/mL |
|---|---|---|---|---|---|
| 1 | oral | 200 | 50 | 2 | 13.7 ± 5.6 |
| 2 | oral | 200 | 50 | 2 | 15.3 ± 9 |
| 3 | oral | 200 | 50 | 2 | 11.1 ± 5.9 |
| 5 | oral | 200 | 50 | 2 | 15.76 ± 3.4 |
| 5 | oral | 200 | 50 | 2 | 5.9 ± 1.9 |
| 5 | oral | 200 | 50 | 2 | 13.6 ± 7.54 |

*AUC = Total $AUC_{0 \to \infty}$
**AUC = $AUC_{0 \to 4h}$

2e. Oral Delivery of human Growth Hormone Releasing Factor Analog (trans-3-henxenoyl hGRF NH$_2$)

Oral dosing (PO) compositions of delivery agent compound and GRF analog g (available from Theratechnologies, Quebec Canada U.S. Pat. Nos. 5,861,379 and 6,020,311) were prepared in deionized water. Typically, 500 mg of delivery agent compound was added to 1.5 ml of water. The free base of the delivery agent compound was converted to the salt by stirring the resultant solution and adding one equivalent of hydrogen chloride. The solution was vortexed, then heated (at about 37° C.) and sonicated. The pH was adjusted to about 7 to 8.5 with NaOH or HCl. Additional NaOH or HCl was added, if necessary, to achieve uniform solubility, and the pH re-adjusted to about 7 to 8.5. Water was then added to bring the total volume to about 2.4 ml and vortexed. About 25 mg of GRF-Analog stock solution (50 mg/ml made from 100 mg GRF-Analog and 2 ml deionized water, adjusting with HCl to pH 4.0) was added to the solution and mixed by inverting. The solution was immediately used in the dosing protocol, or alternatively, the solution was placed into a 37° C. water bath for one hour prior to dosing.

The typical dosing and sampling protocols were as follows. Male Sprague-Dawley rats weighing between about 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=0, 15, 30, 60, & 120 minutes. Plasma GRF-Analog levels were determined by RIA (first antibody Peninsula Labs, RIN 8061; second antibody Linco Research Labs, 5060-10). Plasma GRF-Analog concentrations (pg/ml) were measured for each time point for each of the five animals in each dosing group. The five values for each time point were averaged and the results plotted as plasma GRF-analog concentration versus time. The maximum (peak) are reported below in Table 6.

2f. Interferon—Oral Delivery

Dosing solutions of delivery agent compound and interferon alfacon-1 (IFN) (available as Infergen® from InterMune, Inc. of Brisbane, Calif.) were prepared in deionized water. The free acid of the delivery agent compound was converted to the sodium salt with one equivalent of sodium hydroxide. Typically, a solution of the delivery agent compound was prepared in water and stirred, adding one equivalent of sodium hydroxide (1.0 N) when making the sodium salt. This mixture was vortexed and placed in a sonicator (about 37° C.). The pH was adjusted to about 7.0 to 8.5 with aqueous NaOH. The mixture was vortexed to produce a uniform suspension or solution, also using sonication and heat if necessary. Additional NaOH was added, if necessary, to achieve uniform solubility, and the pH re-adjusted to about 7.0 to 8.5. The delivery agent compound solution was mixed with an IFN stock solution (about 22.0 to 27.5 mg/ml in phosphate buffered saline) and diluting to the desired volume (usually 3.0 ml). The final delivery agent compound and IFN doses, and the dose volumes are listed below in Table 6.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=0, 15, 30, 45, 60 and 90 minutes. Serum IFN concentrations were quantified using Cytoscreen Immunoassay Kit for human IFN-alpha (catalog # KHC4012 from Biosource International, Camarillo, Calif.). Previous studies indicated baseline values of about zero. Results from the animals in each group were averaged for each time point. The maximum of these averages (i.e., the mean peak serum IFN concentration) is reported below in Table 6.

TABLE 5 human Growth Hormone Releasing Factor analog (trans-3-henenoyl hGRF NH$_2$) Delivery

| Delivery Agent Compound | Route of dosing | Delivery Agent Compound Dose (mg/kg) | hGRF Dose (mg/kg) | Volume dose (mL/kg) | Mean plasma Cmax ± SD, µg/mL |
|---|---|---|---|---|---|
| 1 (Citrate) | oral | 200 | 10 | 2 | 194 ± 388 |
| 1 (Mesylate) | oral | 200 | 10 | 2 | $1.21 \times 10^5 \pm 1.45 \times 10^5$ |
| 1 (Mesylate) | oral | 200 | 10 | 2 | $1.84 \times 10^4 \pm 4544$ |
| 1 (Mesylate) | oral | 200 | 10 | 2 | $1.39 \times 10^4 \pm 5237$ |
| 1 (Mesylate) | oral | 200 | 10 | 2 | $2.69 \times 10^5 \pm 1.19 \times 10^4$ |
| 2 | oral | 200 | 10 | 2 | $1.57 \times 10^5 \pm 1.37 \times 10^5$ |
| 2 | oral | 200 | 10 | 2 | $1.92 \times 10^5 \pm 1.66 \times 10^5$ |
| 2 | oral | 200 | 10 | 2 | $1.46 \times 10^5 \pm 1.26 \times 10^5$ |
| 3 | oral | 200 | 10 | 2 | 781 ± 1469 |
| 3 | oral | 200 | 10 | 2 | $1.43 \times 10^5 \pm 1.19 \times 10^5$ |
| 3 | oral | 200 | 10 | 2 | $2.28 \times 10^5 \pm 1.09 \times 10^5$ |
| 3 | oral | 200 | 10 | 2 | $2.10 \times 10^4 \pm 1.53 \times 10^4$ |
| 5 | oral | 200 | 10 | 2 | 22,709 ± 13,067 |
| 5 | oral | 200 | 10 | 2 | $1.78 \times 10^4 \pm 3.20 \times 10^4$ |
| 5 | oral | 200 | 10 | 2 | 4911 ± 3250 |
| 5 | oral | 200 | 10 | 2 | $1.43 \times 10^4 \pm 1.39 \times 10^4$ |
| 5 | oral | 200 | 10 | 2 | $8.12 \times 10^4 \pm 1.63 \times 10^5$ |
| 10 | oral | 200 | 10 | 2 | 3848 ± 995 |

TABLE 6

Interferon - Oral Delivery

| Delivery Agent Compound | Delivery Agent Compound Dose (mg/kg) | IFN Dose (mg/kg) | Volume dose (ml/kg) | Mean Peak Serum [IFN] (ng/ml) ± SD |
|---|---|---|---|---|
| 8 | 200 | 1 | 1 | 0 ± 0 |

The above mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A compound selected from

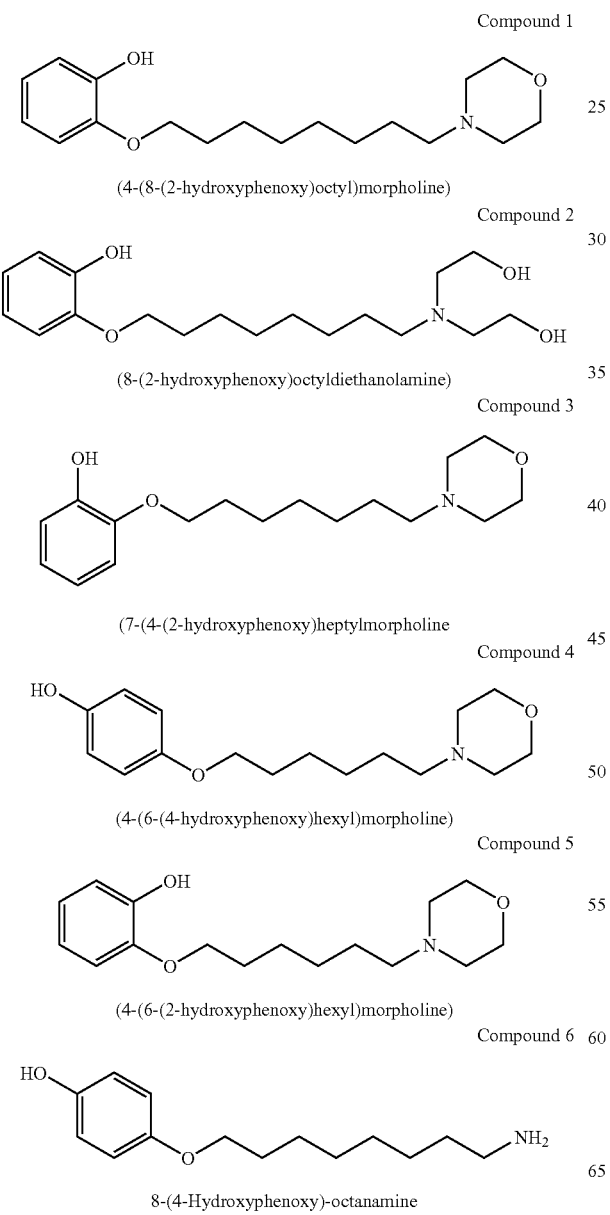

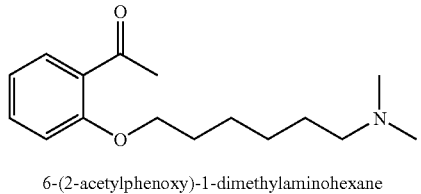

6-(2-acetylphenoxy)-1-dimethylaminohexane

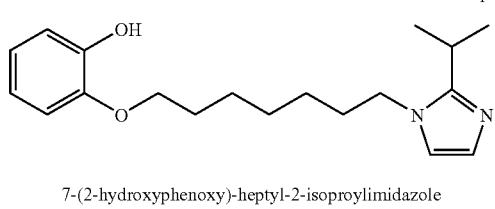

7-(2-hydroxyphenoxy)-heptyl-2-isproylimidazole

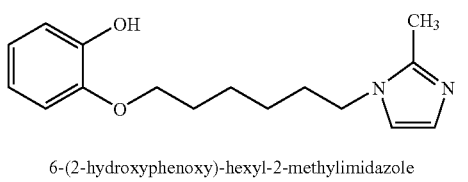

6-(2-hydroxyphenoxy)-hexyl-2-methylimidazole

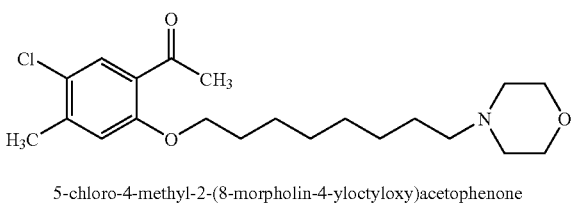

5-chloro-4-methyl-2-(8-morpholin-4-yloctyloxy)acetophenone and salts thereof.

2. A composition comprising:
   (A) an active agent; and
   (B) at least one compound according to claim 1 or a salt thereof.

3. The composition of claim 2, wherein the active agent is selected from the group consisting of a biologically active agent, a chemically active agent, and a combination thereof.

4. The composition of claim 3, wherein the biologically active agent comprises at least one protein, polypeptide, peptide, hormone, polysaccharide, mucopolysaceharide, carbohydrate, or lipid.

5. The composition of claim 3, wherein the biologically active agent is selected from the group consisting of: BJBN-4096BS, growth hormones, human growth hormones recombinant human growth hormones (rhGH), bovine growth hormones, porcine growth hormones, growth hormone releasing hormones, growth hormone releasing factor, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoeitin, filgrastim. postaglandins, cyclosporin, vasopressin, cromolyn sodium, sodium chromoglycate, disodium chromoglycate, vancomycin, desferrioxamine (DFO), parathyroid hormone (PTH), fragments of PTH, antimicrobials, anti-fungal agents, vitamins; analogs, fragments, mimetics and polyethylene glycol (PEG)-modified derivatives of these compounds; and any combination thereof.

6. The composition of claim 3, wherein the biologically active agent comprises insulin, BIBN-4096BS, calcitonin, parathyroid hormone, erythropoietin, growth hormones or combinations thereof.

7. The composition of claim 3, wherein the biologically active agent comprises BIBN-4096BS.

8. The composition of claim 3, wherein the biologically active agent comprises insulin.

9. A dosage unit form comprising:
(A) the composition of claim 6; and
(B) (a) an excipient,
   (b) a diluent,
   (c) a disintegrant,
   (d) a lubricant,
   (e) a plasticizer,
   (f) a colorant,
   (g) a dosing vehicle, or
   (h) any combination thereof.

10. The dosage unit form of claim 9, wherein the active agent is selected from the group consisting of a biologically active agent, a chemically active agent, and a combination thereof.

11. The dosage unit form of claim 10, wherein the biologically active agent comprises at least one protein, polypeptide, peptide, hormone, polysaccharide, mucopolysaccharide, carbohydrate, or lipid.

12. The dosage unit form of claim 10, wherein the biologically active agent is selected from the group consisting of: BIBN-4096BS, growth hormones, human growth hormones (hGH), recombinant human growth hormones (rhGH), bovine growth hormones, porcine growth hormones, growth hormone releasing hormones, growth hormone releasing factor, interferons, α-interferon, β-interferon, γ-interferon, interleukin-1, interleukin-2, insulin, porcine insulin, bovine insulin, human insulin, human recombinant insulin, insulin-like growth factor, insulin-like growth factor-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin, atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoeitin, fllgrastim. postaglandins, cyclosporin, vasopressin, cromolyn sodium, sodium chromoglycate, disodium chromoglycate, vancomycin, desferrioxamine, parathyroid hormone, fragments of PTH, antimicrobials, anti-fungal agents, vitamins; analogs, fragments, mimetics and polyethylene glycol-modified derivatives of these compounds; and any combination thereof.

13. The dosage unit form of claim 10, wherein the biologically active agent comprises insulin, BJBN-4096BS, calcitonin, parathyroid hormone, erythropoietin, human growth hormones or combinations thereof.

14. The dosage unit form of claim 9, wherein the active agent comprises recombinant BIBN-4096BS.

15. The dosage unit form of claim 9, wherein the active agent comprises insulin.

16. The dosage unit form of claim 9, wherein the dosage unit form comprises a dosing vehicle comprising a tablet, a capsule, a powder, or a liquid.

17. The dosage unit form of claim 9, wherein the dosing vehicle is a liquid selected from the group consisting of water, 1,2-propane diol, ethanol, and any combination thereof.

18. A method for administering a biologically-active agent to an animal in need of the agent, the method comprising administering orally to the animal the composition of claim 3.

19. The composition of claim 2, wherein the active agent is a bisphosphonate.

20. The composition of claim 19, wherein the bisphosphonate is selected from alendronate, tiludronate, etidronate, clodronate, pamidronate, olpadronate, incadronate, and mixtures thereof.

21. The compound of claim 1, wherein the compound is

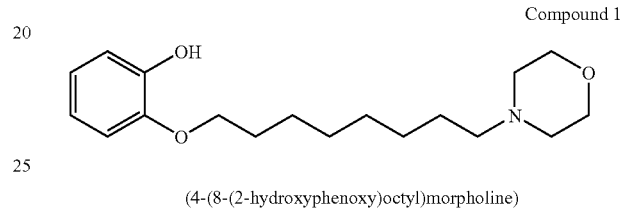

(4-(8-(2-hydroxyphenoxy)octyl)morpholine)

Compound 1 or a salt thereof.

22. The compound of claim 1, wherein the compound is

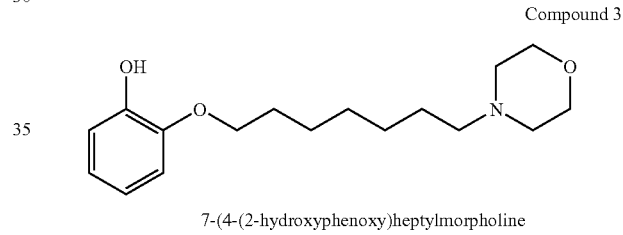

7-(4-(2-hydroxyphenoxy)heptylmorpholine

Compound 3 or a salt thereof.

23. The compound of claim 1, wherein the compound is

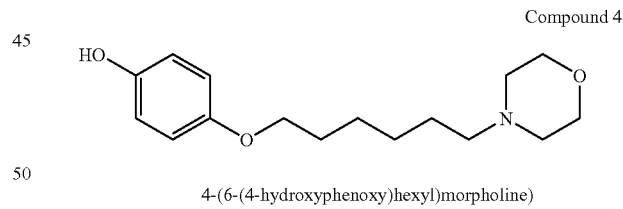

4-(6-(4-hydroxyphenoxy)hexyl)morpholine)

Compound 4 or a salt thereof.

24. The compound of claim 1, wherein the compound is

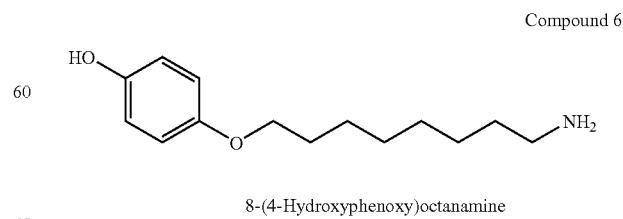

8-(4-Hydroxyphenoxy)octanamine

Compound 6 or a salt thereof.

25. The compound of claim 1, wherein the compound is

Compound 8

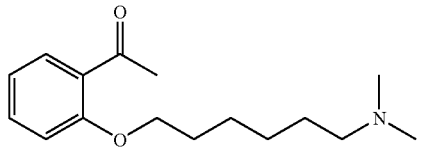

6-(2-acetylphenoxy)-1-dimethylaminohexane or a salt thereof.

26. The compound of claim 1, wherein the compound is

Compound 9

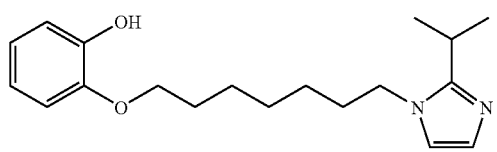

7-(2-hydroxyphenoxy)-heptyl-2-isoproylimidazole or a salt thereof.

27. The compound of claim 1, wherein the compound is

Compound 10

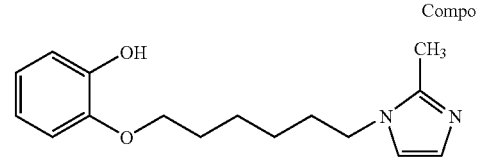

6-(2-hydroxyphenoxy)-hexyl-2-methylimidazole or a salt thereof.

28. The compound of claim 1, wherein the compound is

Compound 11

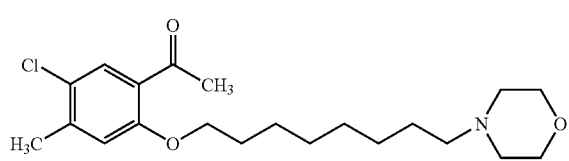

5-chloro-4-methyl-2-(8-morpholin-4-yloctyloxy)acetophenone or a salt thereof.

29. The composition of claim 5, wherein the compound in (B) is

Compound 1

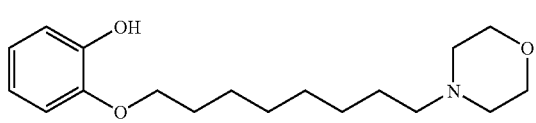

(4-(8-(2-hydroxyphenoxy)octyl)morpholine)

or a salt thereof.

30. The composition of claim 5, wherein the compound in (B) is

Compound 3

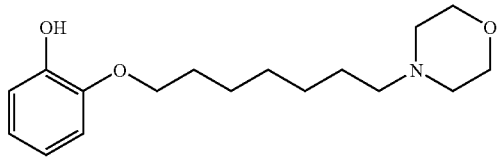

7-(4-(2-hydroxyphenoxy)heptylmorpholine or a salt thereof.

31. The composition of claim 5, wherein the compound in (B) is

Compound 4

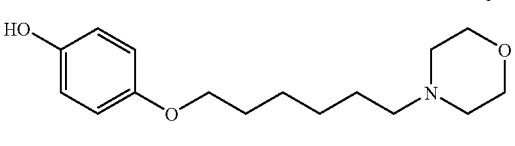

4-(6-(4-hydroxyphenoxy)hexyl)morpholine)

or a salt thereof.

32. The composition of claim 5, wherein the compound in (B) is

Compound 6

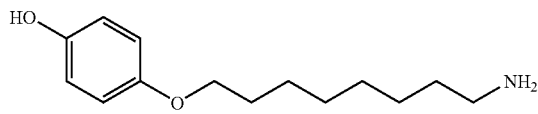

8-(4-Hydroxyphenoxy)octanamine or a salt thereof.

33. The composition of claim 5, wherein the compound in (B) is

Compound 8

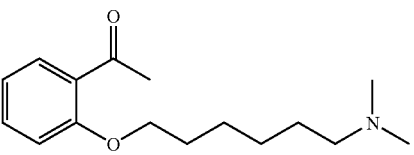

6-(2-acetylphenoxy)-1-dimethylaminohexane or a salt thereof.

34. The composition of claim 5, wherein the compound in (B) is

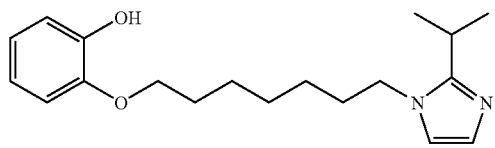

Compound 9

7-(2-hydroxyphenoxy)-heptyl-2-isoproylimidazole or a salt thereof.

35. The composition of claim 5, wherein the compound in (B) is

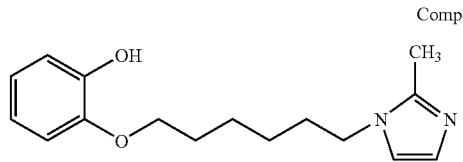

Compound 10

6-(2-hydroxyphenoxy)-hexyl-2-methylimidazole or a salt thereof.

36. The composition of claim 5, wherein the compound in (B) is

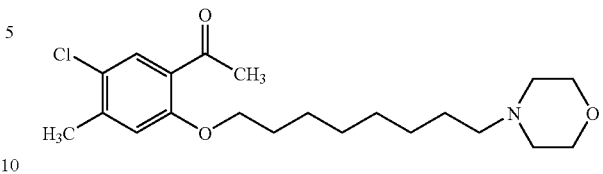

Compound 11

5-chloro-4-methyl-2-(8-morpholin-4-yloctyloxy)acetophenone or a salt thereof.

37. 8-(2-hydroxyphenoxy)octyldiethanolamine or a salt thereof.

38. 4-(6-(2-hydroxyphenoxy)hexyl)morpholine or a salt thereof.

39. A pharmaceutical composition comprising:
(A) an active agent; and
(B) 8-(2-hydroxyphenoxy)octyldiethanolamine or a salt thereof.

40. The pharmaceutical composition of claim 39, wherein the active agent is a bisphosphonate.

41. The composition of claim 40, wherein the bisphosphonate is selected from alendronate, tiludronate, etidronate, clodronate, pamidronate, olpadronate, incadronate, and mixtures thereof.

42. The pharmaceutical composition of claim 39, wherein the active agent is erythropoietin.

43. The pharmaceutical composition of claim 39, wherein the active agent is follicle stimulating hormone.

44. A pharmaceutical composition comprising:
(A) an active agent; and
(B) 4-(6-(2-hydroxyphenoxy)hexyl)morpholine or a salt thereof.

* * * * *